US00PP15028P3

(12) United States Plant Patent
Pecota et al.

(10) Patent No.: US PP15,028 P2
(45) Date of Patent: Jul. 20, 2004

(54) ORNAMENTAL SWEETPOTATO PLANT NAMED 'SWEET CAROLINE LIGHT GREEN'

(50) Latin Name: *Ipomoea batatas*
Varietal Denomination: Sweet Caroline Light Green

(75) Inventors: Kenneth Pecota, Raleigh, NC (US); G. Craig Yencho, Washington, NC (US); Cynthia Pierce, Clayton, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 10/114,386

(22) Filed: Apr. 2, 2002

(65) Prior Publication Data

US 2003/0188359 P1 Oct. 2, 2003

(51) Int. Cl.[7] ..... A01H 5/00
(52) U.S. Cl. ..... Plt./258
(58) Field of Search ..... Plt./258

(56) References Cited

PUBLICATIONS

Armitage, Allan M. and James M. Garner, "*Ipomoea batatas* 'Margarita,'" *HortScience*: 36(1) 178 (Feb. 2001).
Armitage, Allan M., "Sweet Potato," *Greenhouse Grower*: 103–104 (Mar. 1999).
Baggett, "Sweet potato vines are morning glory cousins," *Fine Gardening*: 84 (Apr. 2002).
Bodger Seeds, Ltd., "2001 Pack Trials" invitation, Apr. 3–12, 2001.
Bodger Seeds, Ltd., "2001 Pack Trials" brochure, p. 13, Apr. 3–12, 2001.
Bodger Botanicals catalog, Sep./Oct.: p. 6 (2001).
North Carolina State University, "New Sweet Potatoes Add Ornamental Flavor," *Extension's Successful Garden*: p. 1 (Mar. 2002).
Online catalog selling Ipomea cultivars: www.glasshouse-works.com/trop–ij.html p. 4, date of access: Aug. 15, 2002.
Online catalog selling Ipomea cultivars: www.sunny-field.com/varietylists/companionplants.html p. 5, date of access: Aug. 15, 2002.
Online catalog selling Ipomea cultivars: www.papgen-os.com/plantdb/plants.asp?catid=15 pp. 1–4, date of access: Aug. 15, 2002.
"Ornamental Sweet Potatoes," www.Inla.org/ornpotato.html pp. 1–2, updated Jun. 4, 2000, date of access: Aug. 15, 2002.
"Bodger Seeds/Botanicals," *Greenhouse Grower* (Jun. 2001).

*Primary Examiner*—Kent Bell
(74) *Attorney, Agent, or Firm*—Myers Bigel Sibley & Sajovec, P.A.

(57) ABSTRACT

A new and distinct ornamental cultivar of *Ipomoea batatas* called 'Sweet Caroline Light Green' is described that is a moderately-compact plant with light green leaves that are moderately- to deeply-lobed. The plant is distinguished by its many short shoots, dense foliage, chartreuse leaves, and purple band at the leaf base. Furthermore, this plant has excellent vigor and flowers under short day conditions. *Ipomoea batatas* 'Sweet Caroline Light Green' is suitable for use in landscaping and containerized gardens.

8 Drawing Sheets

Latin name of the genus and species: The Latin name of the novel, ornamental plant variety disclosed herein is *Ipomoea batatas* (L.) Lam.

Variety denomination: The inventive cultivar of *Ipomoea batatas* disclosed herein has been given the variety denomination 'Sweet Caroline Light Green'.

BACKGROUND OF THE INVENTION

Ipomoea species are members of the morning glory family Convolvulaceae. *Ipomoea batatas,* commonly referred to as the white or yellow sweetpotato and the orange yam, are typically fast growing vines with palmately-lobed leaves. These ornamental species produce storage roots identical in appearance to the common sweet potato, but not as palatable. Late in the growing season, tubular flowers appear which are similar to morning glories, but plantings are dominated by the appearance of the foliage. The plants are highly desirable due to their ability to grow under varied stress conditions, cover a large space, and last the entire growing season. Moreover, these plants have few insect or disease problems.

Existing varieties of *Ipomoea batatas* are popular for landscaping applications. There are currently six common types of ornamental sweetpotatoes that are being cultivated primarily for annual, summer vines. These six cultivars are 'Blackie' (unpatented), having dark purple-black foliage, lavender flowers, and edible storage roots; 'Terrace Lime' (unpatented) and 'Margarita' (unpatented; also known as 'Sulfur'), which have large brilliant chartreuse leaves and lavender blooms; 'Black Heart' (unpatented; also known as 'Ace of Spades'), having heart-shaped leaves with burgundy purple color; 'Tricolor' (unpatented; also known as 'Pink Frost'), is a variegated plant which has pale green, white, and pink-margined leaves; and 'Lady Fingers' (unpatented), which has medium green, dainty leaves divided into long, thin, fingerlike lobes which are complemented by burgundy stems and veins.

*Ipomoea batatas* 'Margarita' has recently been released in the United States, and has become widely used as a landscape annual. It is not suitable for mixed containers, as this variety exhibits a very vigorous growth and tends to outcompete other species. Another popular variety is 'Blackie', a vigorous purple-leaved clone which is also unsuited to containerized gardens. See Armitage. A. M. and J. M. Garner, 2001. *Ipomoea batatas* 'Margarita'. *HortScience* 36:178.

Therefore, to meet the current horticultural demand, it is desirable to produce new, more robust cultivars of ornamental sweetpotato with attractive foliage colors, leaf shapes, and plant architectures. In addition, it would be advantageous to develop cultivars of ornamental sweetpotato exhibiting a more compact growth, and which do not out-compete other species in mixed containers.

The present invention comprises a new and distinct variety of *Ipomoea batatas,* which has been named 'Sweet Caroline Light Green'. The variety is suitable for use as a landscape or containerized plant.

Lineage

The *Ipomoea batatas* 'Sweet Caroline Light Green' cultivar originated from a conventional cross between *Ipomoea batatas* cultivars NC15-2ORN (the female parent; not patented) and NC136-4ORN (the male parent; not patented) conducted in the Winter of 1999–2000 at the Horticultural Greenhouses located at North Carolina State University, Raleigh, N.C. NC15-2ORN resulted from a cross between 'Sulfur' and a 'P5' (origin unknown) by 'Sulfur' cross. NC136-4ORN resulted from a cross between 'Sulfur' and a 'Sulfur' by 'Blackie' cross. Seeds from this cross were planted in the Horticultural Greenhouses in Spring 2000. The single, individual plant now known as *Ipomoea batatas* 'Sweet Caroline Light Green' was selected in July 2000 because of its combination of exceptional features, and has been propagated asexually since that time.

Asexual Reproduction

Since its selection, *Ipomoea batatas* 'Sweet Caroline Light Green' has been asexually reproduced at the Horticultural Greenhouses located at North Carolina State University, Raleigh, N.C. predominantly by vegetative propagation of vine cuttings. Asexual propagation of the new cultivar by cuttings at the location previously stated has shown that the unique features of this new Ornamental Sweetpotato are stable and the plant reproduces true to type in successive generations of asexual propagation.

SUMMARY OF THE INVENTION

The present *Ipomoea batatas* 'Sweet Caroline Light Green' ornamental plant is a moderately-compact, densely-mounding cultivar producing many, short shoots and having dense foliage. This cultivar is distinguishable from other cultivars known to the inventors by its bright chartreuse green leaves that have 3–5 moderate to deep-lobes. The plant has a good vigor, but is less vigorous than *Ipomoea batatas* 'Margarita' and 'Blackie' and, unlike these cultivars, 'Sweet Caroline Light Green' may be grown in containers with other species. 'Sweet Caroline Light Green' flowers under short day conditions.

DETAILED BOTANICAL DESCRIPTION

The following is a detailed description of the botanical characteristics of a new and distinct cultivar of *Ipomoea batatas* plant known by the cultivar name 'Sweet Caroline Light Green'. All colors cited herein refer to The Royal Horticultural Society Colour Chart (The Royal Horticultural Society, London, 1995 edition) designations except where general terms of ordinary dictionary significance are used. Where dimensions, sizes, colors, and other characteristics are given, it is to be understood that such characteristics are approximations or averages set forth as accurately as practicable.

The descriptions reported herein are from 12-week-old plants grown individually in six-inch azalea pots. The plants were grown in Lompoc, Calif., under commercial practice in a polycarbonate-covered greenhouse during the 2001–2002 winter season with day and night temperatures ranging between 18.3–26.7° C. and 15.6–18.3° C., respectively, and light levels of about 4,000–8,000 foot-candles. *Ipomoea batatas* 'Sweet Caroline Light Green' has not been observed under all possible environmental conditions, therefore, the phenotype may vary under different environmental conditions such as season, temperature, light intensity, day length, cultural conditions, and the like.

Growth Conditions

*Ipomoea batatas* 'Sweet Caroline Light Green' has excellent vigor, has a moderately fast growth rate, and is very adaptable to container culture. In locales with mild winter conditions, *Ipomoea batatas* 'Sweet Caroline Light Green' will grow perennially; otherwise it is an annual plant that is killed by frost. In the greenhouse setting described above, after twelve weeks of growth, plants of this cultivar produce compact, round-mounded, herbaceous plants averaging 16 cm in height and 40 cm in length. Similar to cultivated sweetpotatoes, wind or rain rarely causes much damage to 'Sweet Caroline Light Green', but if damage does occur, the plant drops the damaged leaves and grows new shoots at nodes where the leaves were lost. Under low light levels in a greenhouse, 'Sweet Caroline Light Green' can develop intumescence, which will remain on the affected foliage, but will be outgrown with new foliage.

Above-Ground Structure and Coloration

Figure 1:
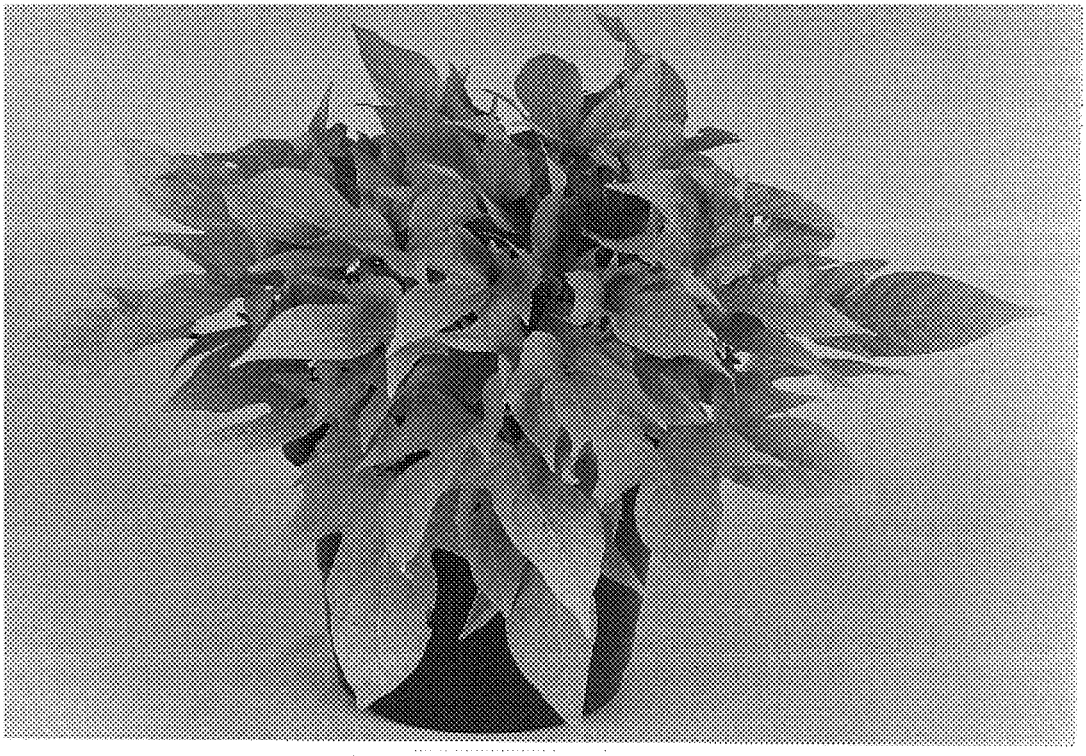
FIG. 1 is a color photograph of a typical plant of the *Ipomoea batatas* 'Sweet Caroline Light Green' grown in a container under commercial greenhouse conditions.
Figure 3:
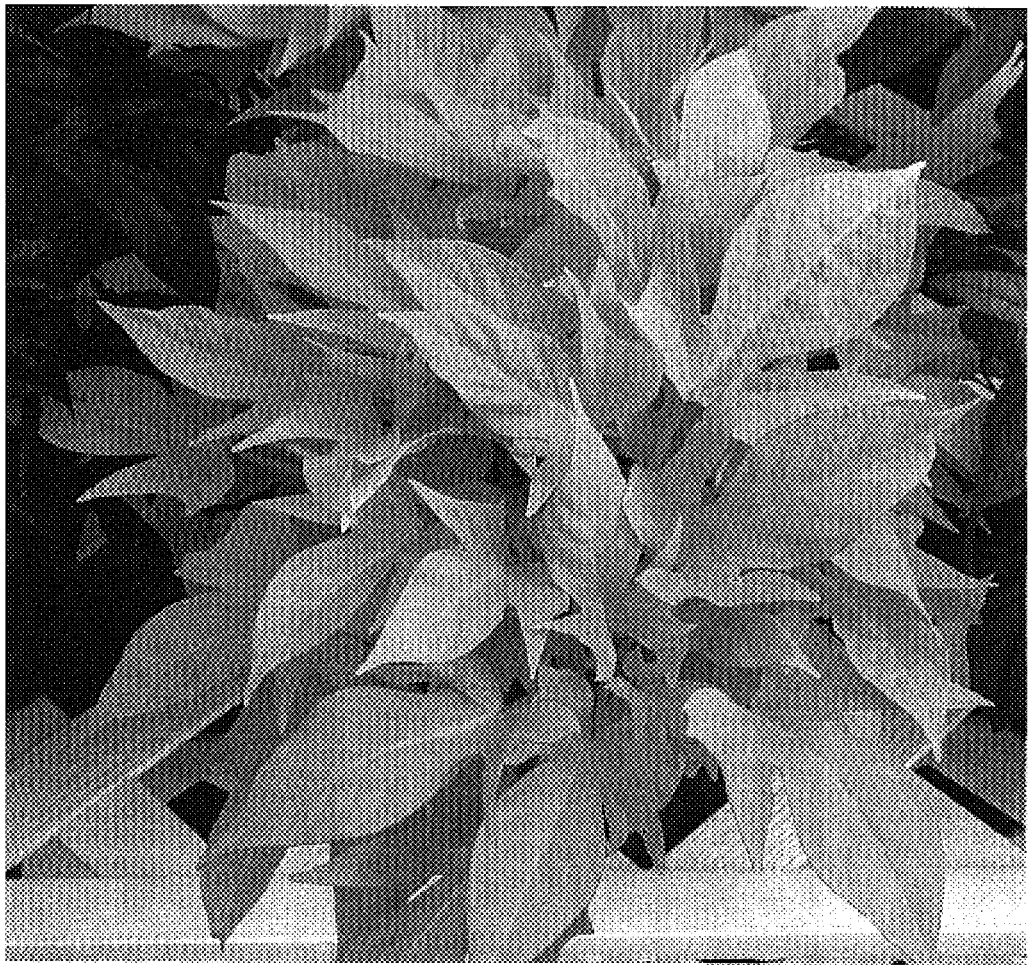
FIG. 3 shows a top view of a typical plant of the *Ipomoea batatas* 'Sweet Caroline Light Green' grown in a container under commercial greenhouse conditions.

FIGS. 1 and 3 show the shape and coloration of typical plants of *Ipomoea batatas* 'Sweet Caroline Light Green'. Overall, this cultivar is a moderately-compact, mound shaped, herbaceous plant that has an average height of 16 cm and an average area of spread of 38×40 cm. The growth habit of this plant is to grow upright with shoots growing outward.

Branching Habitat. Freely-branching with ~14 lateral branches coming off the stem. No basal branching. Very dense foliage with no pinching required to stimulate branching.

Stem (Color: 144C). Round and smooth with an outward and upward bending aspect and very good strength. Length: ~12 cm. Diameter: ~0.4 cm. Internodes are short with an average length of ~1.0 cm.

Vegetative Lateral Branches (Color: 144C). Same as stems for most characteristics. Length: ~12 cm. Diameter: ~0.4 cm. Internodes are short with an average length of ~1.0 cm. Many lateral branches are formed and each axil has latent shoots.

Figure 2:
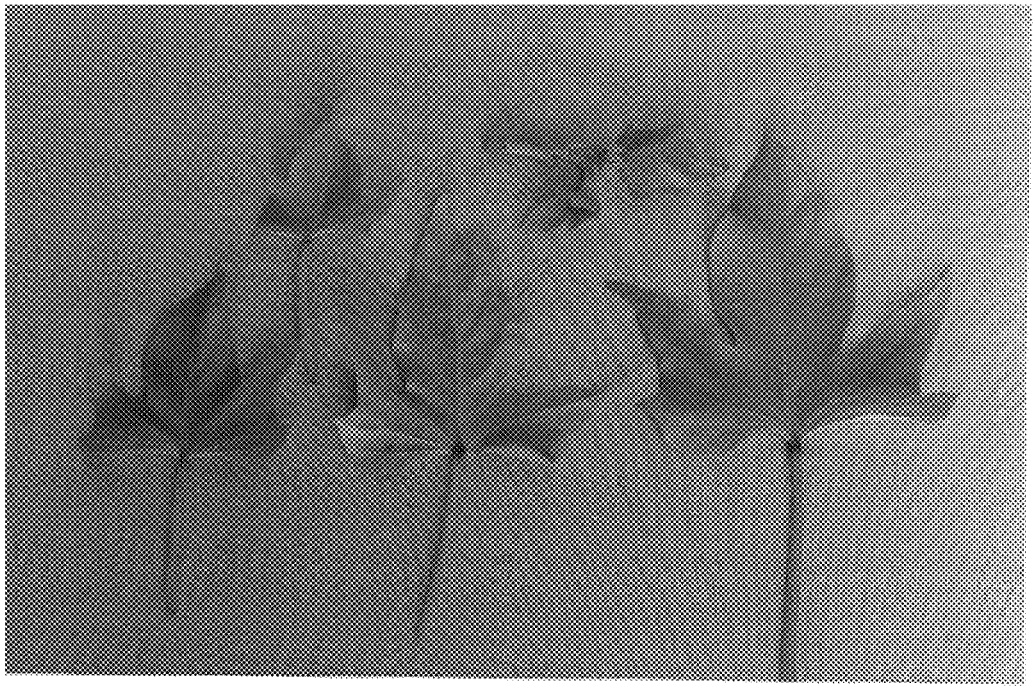
FIG. 2 shows the variety of leaves produced by *Ipomoea batatas* 'Sweet Caroline Light Green' and the lower surface of the leaf (bottom row, center leaf).

Petiole (Color: 145B). Length: ~11.0 cm. Diameter: ~0.3 cm. A very distinct, purple (185B), 0.5 cm band is present at the leaf base at the junction of the petiole with the leaf blade (see FIG. 2).

Foliage. Leaves are alternate and simple. Further, the leaves are palmate and deeply divided into 3–5 lobes. Leaf shape is consistent but size varies (see FIG. 2). Quantity: Very densely foliated, with ~12–14 leaves per lateral branch. Mature leaf length: ~12.4 cm. Mature leaf width: ~10.5 cm. Leaf margin is entire. Lobe width: ~1.8 cm. Mid-vein lobe length: ~9.5 cm. Mid-vein lobe width: ~4.8 cm. Leaf apex: Acute. Leaf base: Acute. Leaf has a smooth texture and matte finish. Venation is palmate at the base with arcuate veins in the center lamina. Color: Table 1. Leaves start out yellow-green and become lighter as they mature.

TABLE 1

| Leaf Structure | Upper Surface | Lower Surface |
|---|---|---|
| Young Leaf | 144B | 144B |
| Mature Leaf | Mixture of 151A and 151B | 145C |
| Vein | 151C | 145D |

Figure 4:
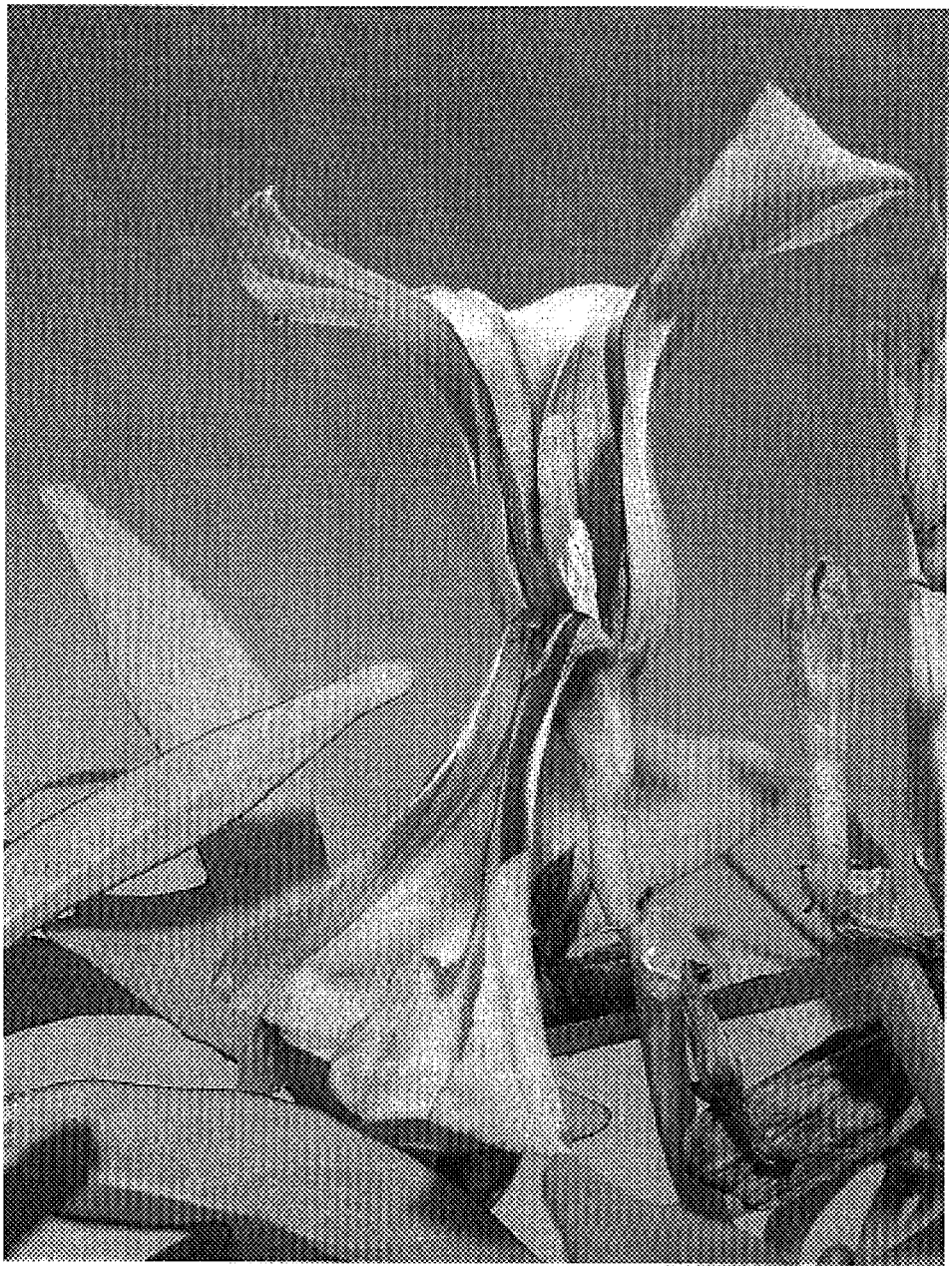
FIG. 4 shows a side view of a flower produced by 'Sweet Caroline Light Green' with a petal peeled back to reveal interior structures.
Figure 5:
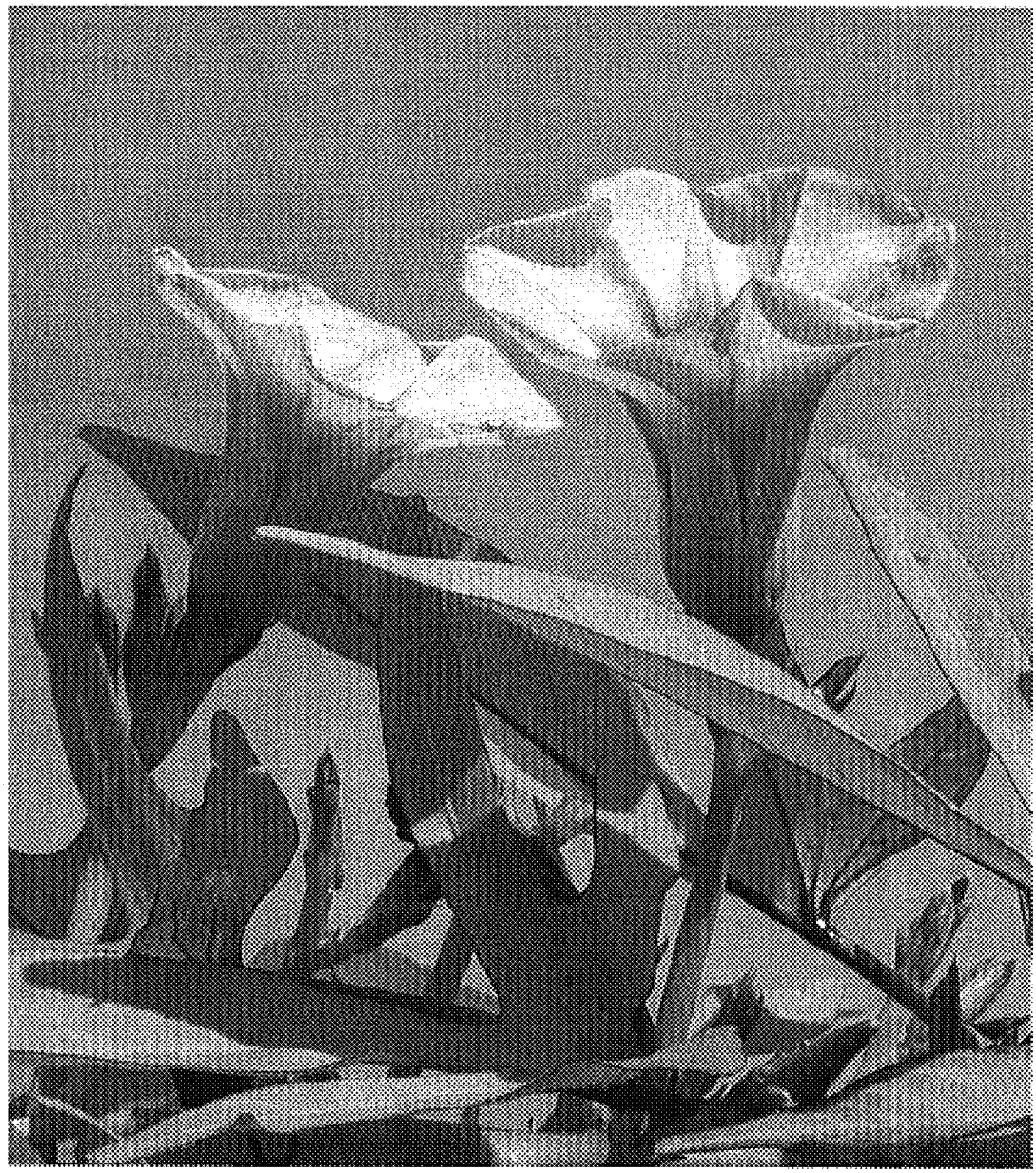
FIG. 5 shows a side view of intact flowers produced by 'Sweet Caroline Light Green'.
Figure 6:
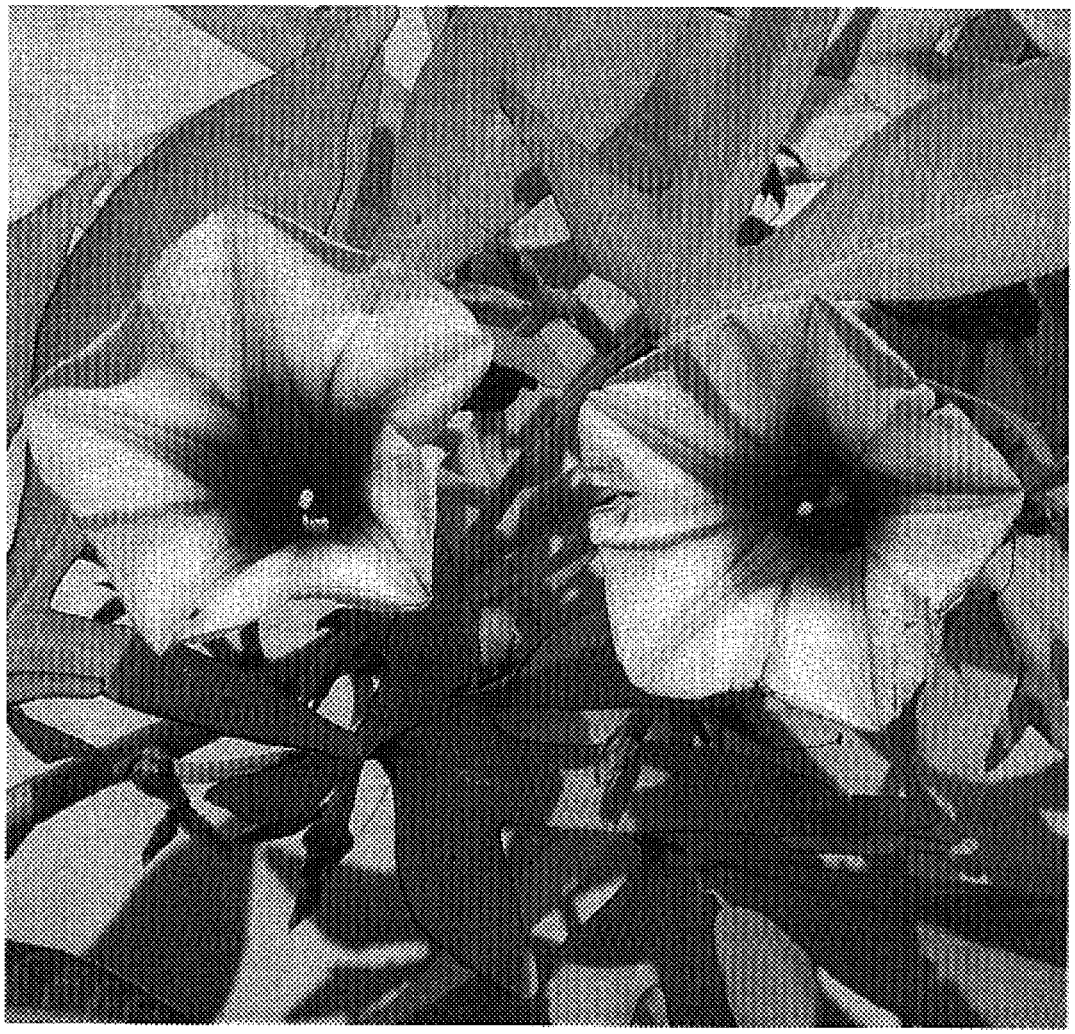
FIG. 6 is a top view of intact flowers produced by 'Sweet Caroline Light Green'.

Flowers. 'Sweet Caroline Light Green' flowers sporadically throughout the season in response to a variety of stressful conditions (e.g., drought, nutrient stress, cloudy weather). Flowering is enhanced by shorter day lengths, but the precise photoperiod for flower induction is currently unknown. FIGS. 4, 5 and 6 show views of typical flowers of the variety. The inflorescence is generally a cyme in which the peduncle is divided into two axillary peduncles. Each peduncle is further divided into two after the flower is produced. Usually buds of the first, second and third order are developed, but sometimes single flowers are produced. The corolla is composed of five fused petals that form a funnel with a round limb. Corolla width: ~4.4 cm, corolla length: ~3.9 cm. The corolla is not fragrant. The limb and outer throat are lavender and the inner throat purple. Inner limb color: 77C, Outer limb color: 77C, Inner throat color: 77A, Outer throat color: 77C. There are five sepals, which are lanceolate and green in color with an acute apex. Each flower has one pistil, with a cream colored style. The stigma is cream colored and has two segments. The stigma is exerted relative to the stamens. The ovary is yellow and superior with two locules that contain one or two ovules. At the base of the ovary there are basal glands containing nectar. There are five cream colored anthers. Pollen is scarce. True seed are not easy to obtain and average less than 1% of the seed set. There is some variation in flower size and color, depending on the environmental conditions. Descriptions are based on: CIP, AVRDC, IBPGR. 1991. Descriptors for Sweet Potato. Huaman, Z., editor. International Board for Plant Genetic Resources, Rome, Italy.

Storage Roots

Figure 8:
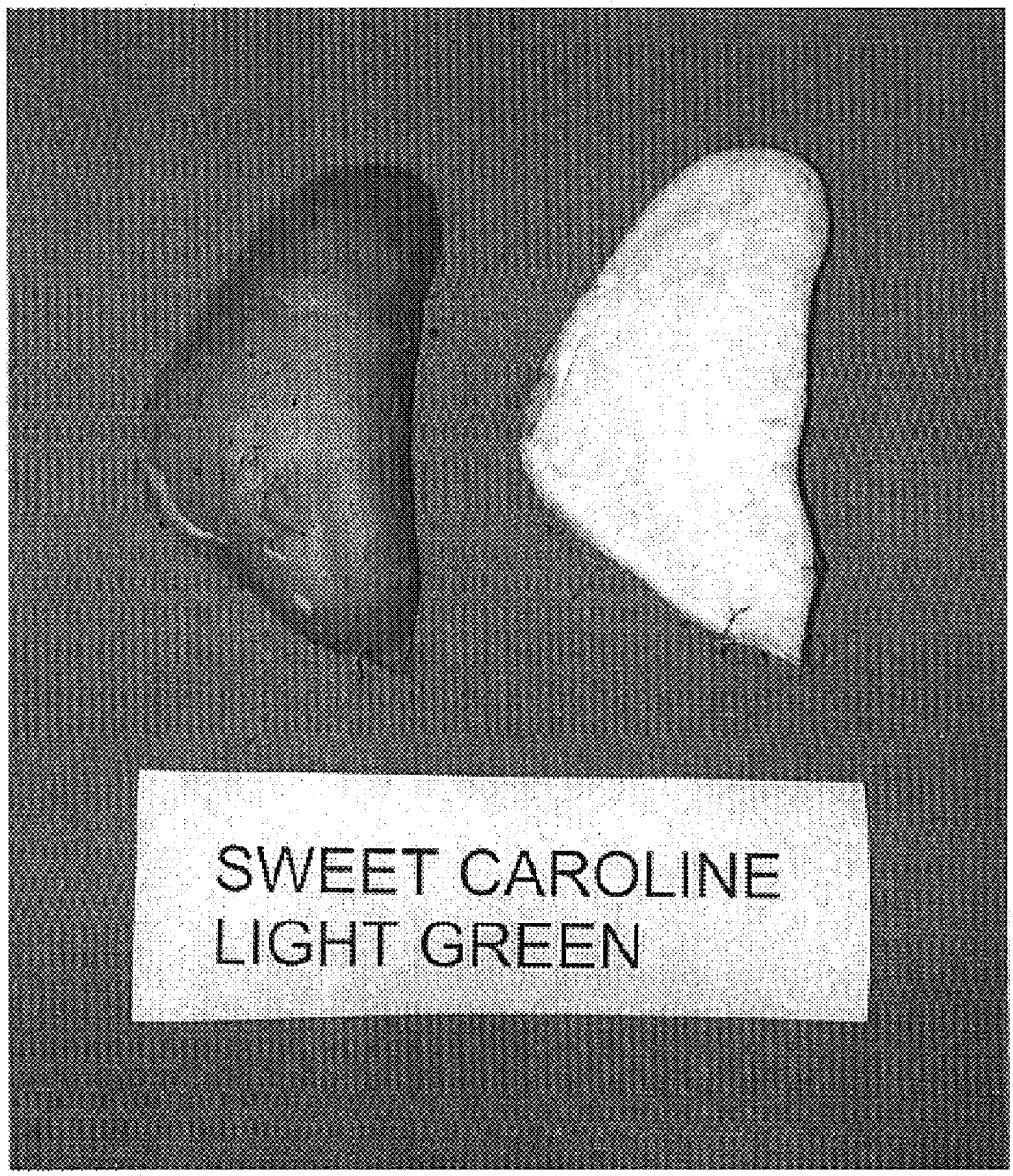
FIG. 8 shows the flesh and skin of a storage root.

As shown in FIG. 8, the storage roots have a light rose skin (Color 186D) and cream-colored flesh (Color: 158B). Shapes are highly irregular and vary considerably in length and diameter depending on growing conditions. A minimum of 130 days are needed to produce storage roots that meet the size criteria for United States Department of Agriculture (USDA) US No. 1 grade (5.1–8.9 cm in diameter and 7.6 to 22.9 cm in length), but very few of these storage roots would meet the shape criteria for US No. 1 grade. Under conditions in which the plant grows perennially, the storage roots will continue to grow as long as the roots are healthy and the weather remains warm.

Comparison With Other *Ipomoea batatas* Cultivars

Figure 7:
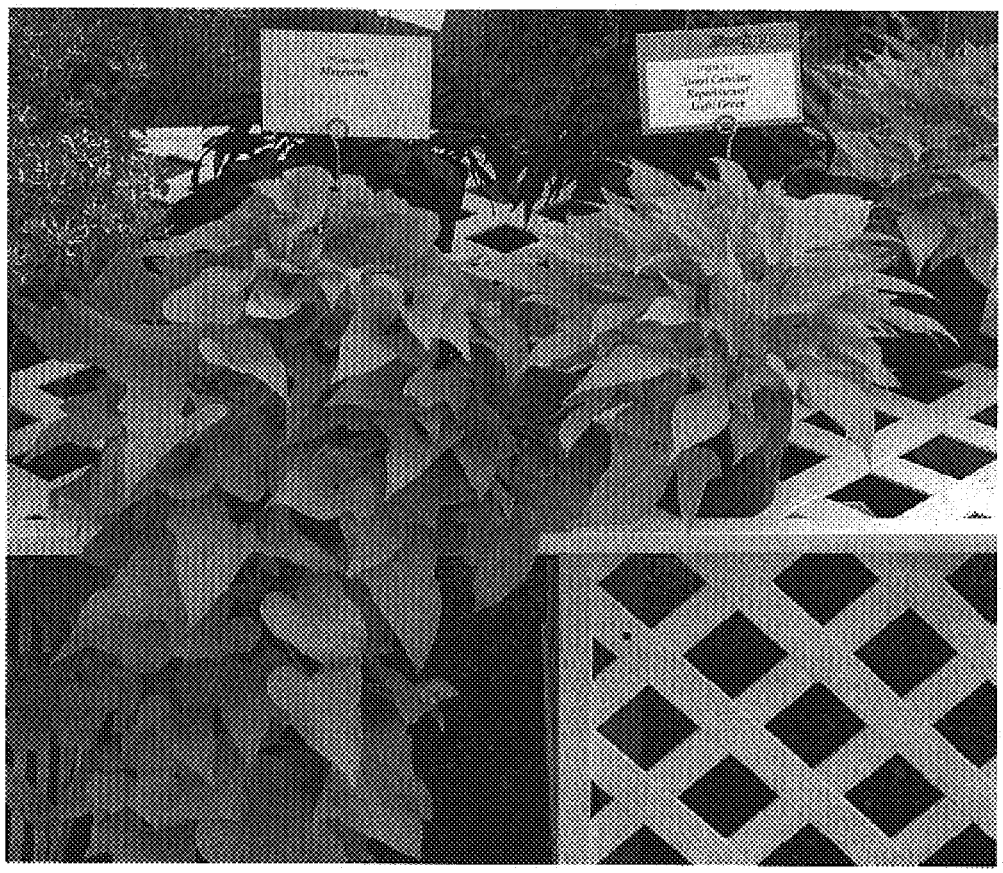
FIG. 7 provides a comparison of *Ipomoea batatas* 'Sweet Caroline Light Green' (right) with the commercially available 'Margarita' cultivar (left).

Of the six most common cultivars of ornamental sweetpotato, *Ipomoea batatas* 'Sweet Caroline Light Green' most resembles the 'Margarita' and 'Terrace Lime' cultivars. Like 'Margarita' and 'Terrace Lime', *Ipomoea batatas* 'Sweet Caroline Light Green' has light green leaves. However, where 'Margarita' and 'Terrace Lime' have large, slightly-lobed leaves, 'Sweet Caroline Light Green' has moderately-sized and moderately- to deeply-lobed leaves. Moreover, 'Sweet Caroline Light Green' has a moderately-compact plant habit as compared with the trailing habit of 'Margarita' (FIG. 7). Furthermore, the storage root of 'Sweet Caroline Light Green' has a light rose skin and cream-colored flesh as compared with the light purple skin and cream-colored flesh of 'Margarita'.

In a comparison with the parental strains, 'Sweet Caroline Light Green' shares attributes with each parent (Table 2), but is also quite distinct therefrom, and comprises a unique combination of characteristics.

TABLE 2

| Characteristic | 'Sweet Caroline Light Green' | Female Parent NC15-2ORN | Male Parent NC136-4ORN |
|---|---|---|---|
| Plant Habit | Moderately Compact | Trailing | Moderately Compact |
| Foliage Color | Light Green | Light Green | Bronze |
| Leaf Size | Moderate | Large | Moderate |
| Leaf Shape | Moderately- to Deeply-Lobed | Slightly-Lobed | Deeply-Lobed |

Disease or Pest Resistance

'Sweet Caroline Light Green' is susceptible to Sweetpotato Feathery Mottle Virus and damage by Japanese beetles.

Herbarium Voucher

A voucher of 'Sweet Caroline Light Green' will be deposited into the Herbarium of North Carolina State University (NCSU) in Raleigh, N.C. upon patenting.

What is claimed is:

1. A new and distinct cultivar of *Ipomoea batatas* plant named 'Sweet Caroline Light Green', substantially as illustrated and described herein.

* * * * *